United States Patent [19]

Carlson et al.

[11] Patent Number: 4,771,629
[45] Date of Patent: Sep. 20, 1988

[54] SYSTEM FOR CHEMICAL ANALYSIS

[75] Inventors: Gerald L. Carlson, Mt. Lebanon Township, Allegheny County; Frederick M. Ryan, Loyalhanna Township, Westmoreland County, both of Pa.

[73] Assignee: Westinghouse Electric Corp., Pittsburgh, Pa.

[21] Appl. No.: 24,297

[22] Filed: Mar. 10, 1987

Related U.S. Application Data

[63] Continuation-in-part of Ser. No. 777,108, Sep. 17, 1985, Pat. No. 4,663,961.

[51] Int. Cl.$^4$ .................... G01N 29/02; G01N 31/08
[52] U.S. Cl. .......................................... 73/23.1; 73/24
[58] Field of Search ............... 250/338, 339, 343; 350/372; 73/23.1, 24, 61.1 C

[56]  References Cited

U.S. PATENT DOCUMENTS

| | | | |
|---|---|---|---|
| 4,051,372 | 9/1977 | Aine | 73/24 |
| 4,490,845 | 12/1984 | Steinbruegge et al. | 250/343 |
| 4,505,550 | 3/1985 | Steinbruegge | 250/339 |
| 4,602,342 | 7/1986 | Gottlieb | 250/339 |
| 4,639,092 | 1/1987 | Gottlieb et al. | 350/372 |
| 4,663,961 | 5/1987 | Nelson et al. | 73/24 |

OTHER PUBLICATIONS

Wiczer et al., "Influence of Electro-Static Field on the Properties of Acoustically Tuned Optical Filters," *Applied Physics*, vol. 30, No. 9 (1977).
G. Schmidke et al., VDI-Berichte 509, 293, (1984), "Nir-Prozeb-specktrometer: Zuzammensetzung von Gasen and Flussigkeiten", pp. 293-295.

*Primary Examiner*—John Chapman
*Assistant Examiner*—Hezron E. Williams
*Attorney, Agent, or Firm*—G. E. Hawranko

[57]  ABSTRACT

An improved system for quantitative chemical analysis incorporates a chromatographic column. A radiation source of a predetermined range of wavelengths is in optical communication with an emerging specie from the chromatographic column by of a first optical path whereby radiation is modified by characteristic of the specie. A detector is in optical communication with the emerging specie by a second optical path whereby a first output signal reflective of the detected radiation is generated. An acousto-optic tunable filter system is disposed in one of either the first or second optical paths. The radiation is passed through the crystal at a predetermined angle relative to the crystal's optic axis. An acoustic transducer is coupled to the crystal to launch acoustic waves into the crystal to interact with a selected narrow bandwidth portion of the radiation to make it distinguishable from the remaining radiation. A computer to which the detector output signal is applied determines the emerging specie by the identifiable characteristics. An auxiliary detector responsive to the emerging specie can be associated with the chromatographic column. A parallel optical path can also be included to define a reference cell. A second output signal reflective of the detected radiation passing through the parallel optical path is generated. The difference between the first and second output signals represents a measure of the emerging specie's absorption characteristic. In an alternative embodiment, an acoustooptic dispersive light filter can be inserted in the system.

33 Claims, 10 Drawing Sheets

SYSTEM FOR CHEMICAL ANALYSIS

CROSS-REFERENCE TO RELATED APPLICATION

This application is a continuation-in-part application of application Ser. No. 777,108, filed on Sept. 17, 1985 which issued as U.S. Pat. No. 4,663,961 on May 12, 1987 and is entitled "A System For Remote Chemical Analysis".

BACKGROUND OF THE INVENTION

1. Field of the Invention

The invention is directed to both a system and a technique for improved quantitative chemical analysis. More particularly, the invention provides for the use of a solid-state acousto-optic device in combination with a chromatographic column in order to provide a system for both the detection and the quantitative chemical analysis of a species of interest.

2. Description of the Prior Art

It is the conventional practice in the petrochemical industry, to utilize "on-line" sensors to affect chemical analysis. However, in such configurations, the presence of electrical or chemical sensors may pose a significant threat to the safety of the area, from either explosions or from chemical contamination. As a result, such "on-line" sensors must be contained in approved explosion-proof enclosures. These enclosures obviously represent a significant cost to the petrochemical industry.

It has been suggested by G. Schmidtke, et al. VDI-Berichte 509,293 (1984) that a fiber-optic system can be utilized to provide remote chemical analysis. This prior art system utilizes a diffraction grating and an array of detectors in a location remote from a sampling area.

The acousto-optic tunable filters (AOTF) has previously been used in spectral analysis as an effective device to measure dilute gas mixtures. An example of an automated AOTF infrared analyzer system which is usable in a variety of industrial and commercial control applications is disclosed in U.S. Pat. No. 4,490,845 to Steinbruegge et al., which patent is assigned to the assignee of the present invention and incorporated herein by reference as if fully set forth.

Concentrated mixtures of gases and especially liquids often have strong, nearly total optical absorption bands. To analyze these mixtures, one must often utilize the weaker overtone absorptions. The overtone bands of infrared absorptions lie in the near-to-intermediate infrared, where quartz fiber-optic attenuation is not prohibitive to the use of such fibers. Using optical fibers eliminates one of the constrains with present detection systems.

The quantitative chemical analysis of mixtures of gases or liquids is greatly simplified by the use of a chromatographic column. The column separates the mixture into its constituent parts by the process of differing diffusion rates of various species through the column. As the various specie emerge from the column they may be quantitatively measured by a variety of techniques, the measurement being greatly simplified by the separation of single emerging specie from others in the original mixture. The columns may be designed to separate various molecular species in liquids, in which case the process is termed "liquid chromatography", or to separate species in a gas mixture, which is termed "gas chromatography". Special variants of these are termed "HPLC, or, High Performance Liquid Chromatography", "Open column liquid chromatography", or "Super critical chromatography", etc.

As the individual specie emerge from the end of the chromatographic column they may be identified and quantified by a number of techniques, the technique chosen to be appropriate for the components of the mixture. Included among these are optical absorption (UV, visible, or IR), fluorescent excitation, refractive index, flame ionization, electrochemical or conductivity. The most commonly used techniques are by far the optical measurement techniques, especially UV absorption. Since the emergence of one specie from the column is followed shortly by another specie, measurements made "on line" at the column must be made quickly or interference between the species will occur and some error in the measurement will result. In many cases the measurement of detailed spectral information requires too much time to allow "on-line" measurements. In these cases the emerging specie is removed from the chromatograph and measured on a separate optical instrument. Much of the thrust in improving chromatographic instruments at the present time is devoted to improving the optical "on-line" detector so that as much information as possible can be obtained without requiring the removal of the specie sample.

A typical example of presently available technology for performing an optical absorption spectral dependence measurement is shown in Prior Art FIG. 12. Broadband light is produced by a discharge lamp "DL", passed through a flow cell "FC" containing the exiting specie to be measured. The spectral dependence of the light absorbed in the flow is analyzed by the combination of a holographic or diffraction grating "DG" and a photodiode array "PA". A lens system "LS" and shutter means "SM" are also illustrated. A similar arrangement would be used for analyzing the spectral dependence of the fluorescence emission of the sample, except that suitable wavelengths for exciting the fluorescence would be employed, and emitted fluorescent light would be analyzed. Additional examples are found in the following U.S. Pat. Nos. the contents of which are incorporated by reference as if fully set forth herein: 4,521,225 to Jenkins et al.; 4,541,269 to Thomas; 3,723,731 to Blau, Jr.; 3,995,960 to Fletcher et al. and 4,501,372 to Aine.

There are several disadvantages of this type of system. The photodiodes are much noisier than a photomultiplier tube detector and the diffraction efficiency of the grating, typically a holographic grating to obtain wide wavelength coverage, is at best 20%. What this means is that the signal/noise level on each detector element is low and the signals must be time averaged to obtain accurate data. The larger the number of diode elements used, the more serious this problem becomes, and the time required to obtain adequate signal/noise output can exceed the time between the arrival of the various species at the flow cell.

It is an object of the present invention to provide a system for chemical analysis which utilizes optical fibers to convey a light source to a sample and then from the sample toward a detector. This configuration would allow the use of such a remote chemical analysis system in applications where the presence of electrical or chemical sensors pose a significant threat from, for example, either explosions or from chemical contamination.

It is yet another object of this invention to provide an improved chemical analyzer which incorporates an automated acousto-optic system.

It is still another object of this invention to provide an improved chromatographic instrument in combination with an acousto-optic device.

It is another object of this invention to provide a method and an apparatus for determining the wavelength dependence of the fluorescence emitted by certain species when excited by light.

It is another object of this invention to determine the excitation spectrum of wavelengths that excite the fluorescence.

SUMMARY OF THE INVENTION

The invention provides an improved system for quantitative chemical analysis which incorporates a chromatographic column means into which a mixture is introduced and through which individual specie of the mixture diffuse at various rates so that each single emerging specie is temporally separated from each other specie and has identifiable characteristics. A radiation source of a predetermined range of wavelengths is in optical communication with the single emerging specie by means of a first optical path whereby radiation from the radiation source is modified by the identifiable characteristics. A detection means is disposed in optical communication with the single emerging specie by means of a second optical path whereby the modified radiation is detected and a first output signal reflective of the detected radiation is generated by the detection means. An acousto-optic tunable filter system, which system comprises an acousto-optic tunable filter having an optically aligned acousto-optic crystal is disposed in one of either the first or second optical paths so as to be in optical alignment therewith such that the radiation is passed through the crystal at a predetermined angle relative to the crystal's optic axis. An acoustic transducer means is coupled to a variable frequency RF energy source and to the crystal to launch acoustic waves into the crystal to interact with a selected narrow bandwidth portion of the radiation to make it distinguishable from the remaining radiation. The selected narrow bandwidth portion is a function of the frequency of the RF energy and the acoustic waves. A computing means to which the detection means output signal is applied for determining the emerging specie by the identifiable characteristics is in electrical communication with the detection means.

The improved system for quantitative chemical analysis can include in an alternative embodiment an auxiliary detector means responsive to the emerging specie and in fluid communication with the chromatographic column means. A parallel optical path can also be included to define a reference cell means whereby radiation passes through both the first and second optical paths and the parallel optical path to the detection means. A second output signal reflective of the detected radiation passing through the parallel optical path is generated. The computing means is also responsive to the second output signal and the difference between the first and second output signals represents a measure of the emerging specie's absorption characteristic. The acousto-optic crystal is also disposed in said parallel optical path. In yet another embodiment, an acousto-optic dispersive light filter can be inserted in the system.

BRIEF DESCRIPTION OF THE DRAWINGS

The above, as well as other features and advantages of the present invention, can be more readily appreciated through consideration of the detailed description of the invention in conjunction with the several drawings in which.

DETAILED DESCRIPTION OF THE INVENTION

Figure 1:
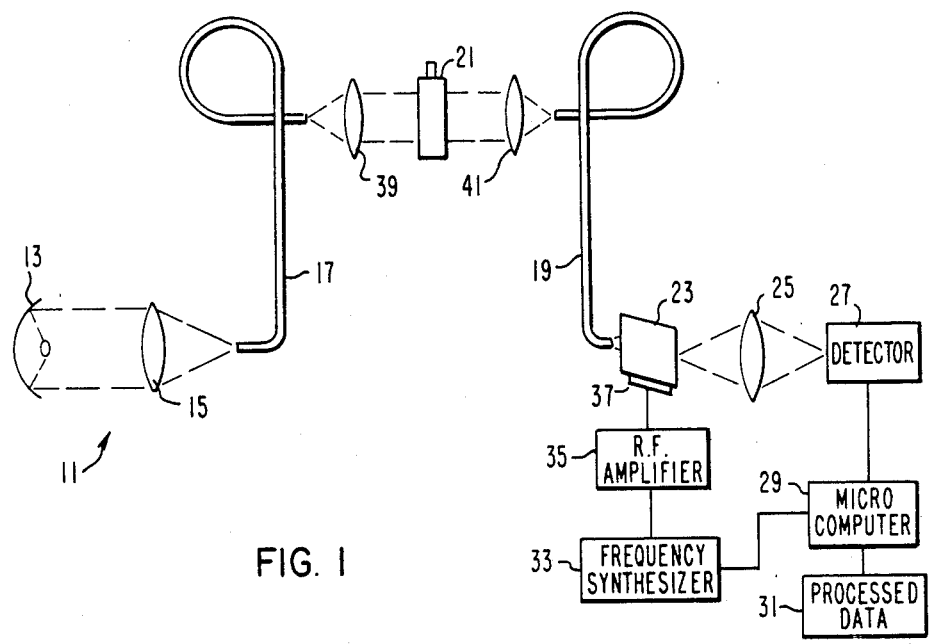
FIG. 1 is a schematic representation of a first embodiment of a remote chemical analysis system all according to the teachings of this invention.

Turning now to FIG. 1, there is shown a block diagram of the expanded system for remote chemical analysis generally indicated by the reference character 11. This system can be visualized in three sections for ease of discussion. The first section contains an infrared source 13 and optics 15 to couple the light into a first optical fiber 17. The second section consists of the first fiberoptic section 17 and a second fiber-optics section 19 as well as a remotely positioned sample cell generally indicated at 21. While a sample cell was utilized in the testing of this system it is to be appreciated that the fiber-optic sections 17 and 19 can be incorporated into a conduit means through which a process stream is conveyed. Accordingly, the term sample cell means is to be understood to include both of the previously described concepts. This sample cell means would be connected through the optical fibers to the infrared source and the infrared detection means. The third section contains the infrared analyzer which includes the acousto-optic tunable filter 23 coupled directly to the optical fiber 19 which conveys the infrared radiation which has been modified by the absorption characteristic of the sample species. Optics as at 25 are disposed between the AOTF 23 and an infrared detector means 27 for focusing the output of the AOTF onto the detector. Support electronics are coupled to the detector and to the AOTF. These electronics include a microcomputer 29, a process data storage means 31, frequency synthesizer 33 and an RF amplifier 35 coupled to the transducer 37 which is in turn, bonded to the acousto-optic crystal. A more detailed description of the electronics package that can be used in combination with an AOTF and infrared detector can be had in U.S. Pat. No. 4,490,845 entitled automated acoustooptic infrared analyzer system, which patent is assigned to the assignee of the present application and which is incorporated herein by reference as if fully set forth.

Figure 2:
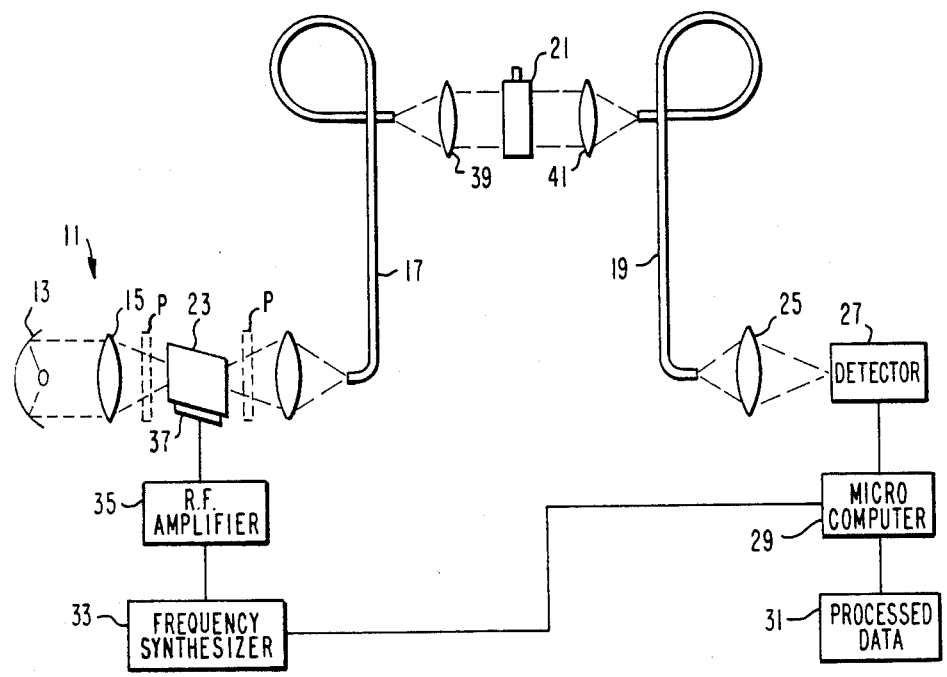
FIG. 2 is a second embodiment of the remote chemical analysis system of this invention in which an acousto-optic tunable filter is disposed on the source side of the sample cell.

As can be seen in FIG. 2, an alternative to the basic configuration described above can be had by incorporating the acousto-optic tunable filter at the source side of the sample cell. In this configuration, the AOTF 23 is disposed between a focusing means 15 for the infrared radiation source 13 and the optical fiber 17. Thus, the only light transmitted through optical fiber 17 is the pulsed light of the desired frequency as will be described hereinafter. This configuration would tend to help improve the signal-to-noise ratio and would be the desired placement for an AOTF based production model. In all other respects, like reference characters represent like components in the configurations of FIGS. 1 and 2. By way of explanation, the embodiment illustrated in FIG. 1 illustrates an actual layout which has been utilized to test the principles of this invention and is better suited to an experimental configuration, for the optics can be more easily aligned. FIG. 2 also includes optional polarizers "P" disposed on either side of the AOTF in dashed line.

In a working model of this invention, the infrared light source 13 was a 2.8 volt, 0.8 amp quartz halogen flashlight bulb mounted in a parabolic reflector. This source proved easy to work with, stable, and produced a well collimated beam. The spectral emission of the bulb adequately covers the range necessary to implement this invention. The light from the beam was focused down into the end of an optical fiber by means of a 2-inch diameter calcium fluoride lens 15. The optical fibers and sample cell constitute the second section described above. The fibers used in the demonstration model were two 18-inch sections of a commercially available 1 mm quartz fiber. The length of the fiber used was sufficient to demonstrate the capabilities of this concept but short enough so that fiber attenuation had little or no effect on the total system response. A sample cell was connected between those two fibers 17 and 19. Calcium fluoride lenses were used to collimate the light input from one fiber and to refocus it onto the other. These lenses were generally indicated by the reference characters 39 and 41, respectively. Within this region of collimated light was a cell 21 to hold the species of interest. The cell consisted of two 4 mm thick sapphire windows separated by a 2 mm neoprene O-ring with an opening in the top thereof to allow a syringe to introduce and remove liquid into and from the cell 21. The area of the cell exposed to the light was approximately 10 $cm^2$ to give a total volume examined of approximately 2 cc. In further tests of this concept, the lens assembly comprising lenses 39 and 41 has been replaced by two plano-convex quartz lenses attached directly to the sapphire windows of the cell 21. This arrangement minimizes alignment difficulties. The light having been modified by the absorptive characteristics of the species contained within the cell is brought back from the cell 21 to the analysis system consisting of the AOTF, detector means, etc. by means of the quartz fiber 19. The working model of this remote chemical analyzer utilized an Apple II microcomputer to interface the TAS AOTF with the support electronics and to enable through an analog-to-digital converter, the collection and storage of data from the infrared detector means 27. The support electronics referred to herein and described in detail by the referenced U.S. Patent, are used to supply pulsed RF drive to the AOTF 23 and consist of a low power frequency synthesizer capable of generating RF output up to 150 MHz, an electronic gate to pulse the signal to the amp, and a high power RF amplifier.

During testing, the AOTF was driven by a 10 s pulse at a duty cycle of 1%. The final peak-to-peak voltage across the transducer was approximately 30 volts. The maximum strength of the diffracted light arrived at the detector 5 s after the pulse ended, at which time the computer recorded the data from the detector. The frequency synthesizer scanned the range from 80 MHz to 130 MHz in 200 KHz steps. At each step, 255 samples were taken from the detector and averaged to minimize system noise. The data for the entire scan was then stored in a disk file and could be plotted to give the spectral response of the system and the sample.

Figure 13:
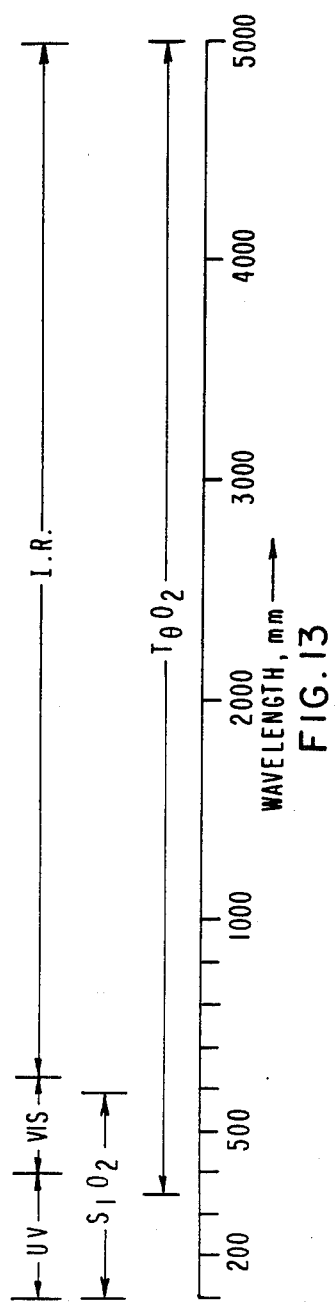
FIG. 13 demonstrates the wavelength coverage possible with two typical AOTF materials.

An AOTF is a solid state spectrometer that can perform spectral analysis. The tuning function is obtained by utilizing special materials that allow the interaction of acoustic waves with light waves to produce a selective diffraction process. FIG. 13 shows the wavelength coverage for two of the materials that would be useful for optical detector elements in combination with chromatographic columns. An AOTF constructed from crystalline quartz ($SiO_2$) could be used to cover the range of from below 200 nm in the UV to around 700 nm in the near IR. $TeO_2$ AOTF's could be used to cover the range of from 350 nm to about 5 micrometers. A typical AOTF design utilizing quartz is shown on FIG. 14, which shows a design described by Chang in 1974 (I.C. Chang, Applied Physics Letters 25, 323, 1974). The advantages of AOTF's over the conventional optical detector designs are the following:

1. High optical throughput. Diffraction efficiencies of 100% are possible and limiting apertures such as the slits used with a grating design are not required.

2. The fast electronically controlled switching times allow wavelength selection to be changed in a matter of microseconds.

3. A single photomultiplier detector can be used. Coupling the superior signal/noise of the PM compared to diodes with the high optical throughput of the AOTF will allow faster spectral measurements of higher spectral detail to be performed.

4. The AOTF can be made smaller in 2 of its 3 dimensions without sacrificing spectral resolution. The small flow cell dimensions typical of chromatographs would be compatible with a small AOTF and allow the use of an inexpensive device.

5. The higher spectral resolution possible would eliminate the need to remove samples to an external spectrophotometer for spectral analysis, saving operator time.

The system illustrated in FIGS. 1 and 2 utilizes a non-collinear thallium arsenic selenide ($Tl_3AsSe_3$ or TAS), AOTF to perform spectral analysis and a lead selenide detector, both interfaced with the aforedescribed microcomputer. The acousto-optic tunable filter can also utilize a TeO₂ crystal or crystalline quartz. Under microcomputer control this equipment gathered and interpreted the transmission spectra. The microcomputer interface provided rapid random access to the RF frequency driving the AOTF, which selected the wavelength of light examined, and also provided routines for sample averaging and the comparison of various reference spectra. The number of liquids and gases both organic and inorganic, with overtone absorptions in the near and intermediate infrared allows this device to cover a wide range of applications. The tunable nature of the AOTF allows the implementation of relatively simple or potentially complex algorithms for analyzing spectra. Also possible is the ability to switch quickly to an alternate range of absorptions at higher concentrations for more accuracy.

Figure 4:
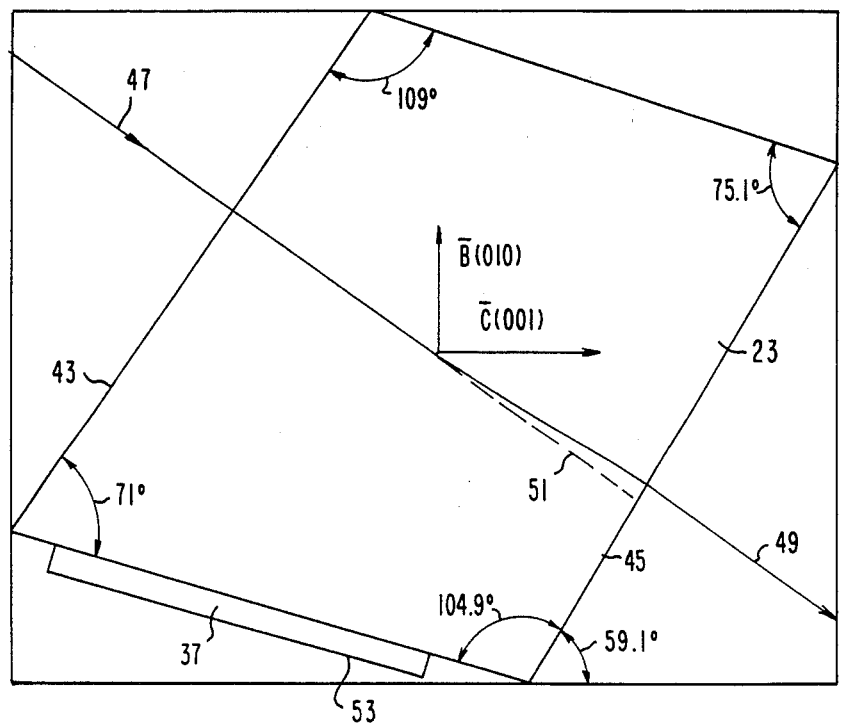
FIG. 4 is a comprehensive illustration of the design of an acousto-optic tunable filter used in an embodiment of this invention.

A small TAS crystal was cut and polished for use as an AOTF in this system. A rather schematic illustration of this TAS crystal is shown in FIG. 4. The TAS crystal was selected for use because of its good transmission in the infrared from 1.3 to 17.0 micrometers and its relatively high acousto-optic "figure of merit". The filter is designed to work in the non-collinear mode of operation, in which the incident light propagates at an angle to the acousto-wave front in the crystal. Although non-collinear AOTF's generally have a lower resolution than collinear filters, the spectra of concentrated gases and liquids are sufficiently broad that the reduced resolution in the non-collinear mode is still acceptable. The non-collinear AOTF also provides a spatial separation between the beam diffracted by the acoustic waves and the light transmitted straight through, thus simplifying the gathering of the light transmission data. The small crystal employed has a large angular aperture for the input light, and could capture the light supplied by a fiber directly attached to the crystal without the need for intermediate optics.

As can be seen in FIG. 4, the cross-section of the crystal 23 is a distorted parallelogram. The slant of the crystal properly orients the input face 43 and the output face 45 of the crystal to the path of the light 47, and allows for acoustic beam walkoff. The input face 43 was designed to be normal to the incident light from the fiber, i.e., 47, and the output face 45 was designed so that the diffracted light emerges parallel to the incident light, but displaced on the order of 1 mm. The deflected signal is indicated at 49 while that light which is not affected through acoustic interaction is indicated by the dashed line 51.

A 30 rotated x-cut lithium niobate crystal plate was indium bonded to the crystal under pressure to the surface of the crystal to serve as the transducer 37. A gold electrode was deposited on top of this at 53 and gold wire bonds connected the transducer by an appropriate connector. The resolution of the filter is determined, among other parameters, by the interaction length between the light and the acoustic path. In the crystal illustrated, that is approximately equal to the length of the transducer which is 5 mm.

Figure 3:
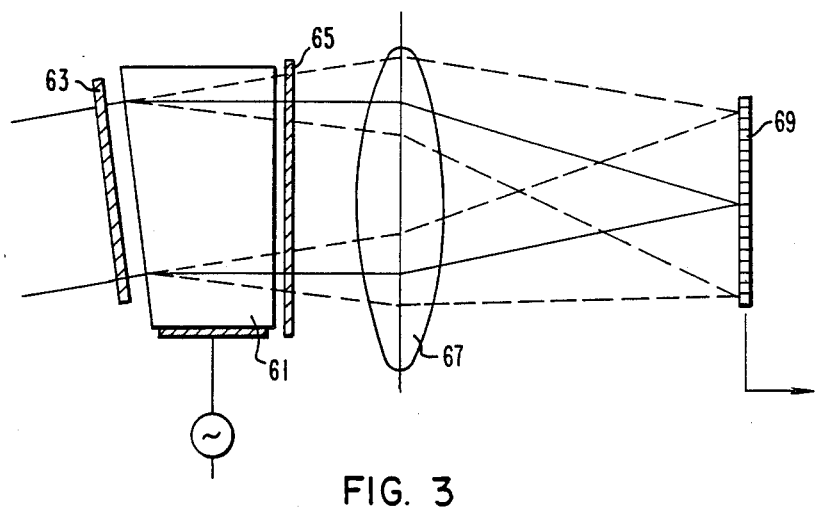
FIG. 3 is a schematic view of the detection scheme of a further alternative embodiment of this invention incorporating the acousto-optic dispersive light filter AODLF.

The alternative embodiment illustrated in FIG. 3 incorporates the acousto-optic dispersive light filter and detector array in lieu of the previously described acousto-optic tunable filter and detector for the AOTF and detector shown in FIG. 1. The acousto-optic dispersive light filter 61 is an electronically adjustable spectroscopic device capable of instantaneously monitoring many wavelengths with a fixed drive frequency. The AODLF is functionally very similar to a fixed grating, but there are several important differences which are advantageous. The two principle differences are the tunability of the AODLF and its birefringent operation. The AODLF is unique in that it allows for the electronic tunability of the grating constant, which allows flexibility of operations, such as large changes of spectral range. The electronic tunability also easily permits the frequency modulation of the optical signal in order to perform derivative spectroscopy, which may improve the signal-to-noise ratio over that of a constant signal. The schematic representation of the spectrum analyzer utilizing the AODLF as shown in FIG. 3 (in combination with FIG. 1) includes input and output polarizers 63 and 65 respectively, a focusing lens 67 and a photodetector array 69 for measuring the spectral information. A thallium arsenic selenide acousto-optic dispersive light filter is described in U.S. patent application Ser. No. 666,416 filed Oct. 30, 1984 which issued as U.S. Pat. No. 4,639,092 on Jan. 27, 1987, is assigned to the assignee of the present invention and is incorporated herein by reference as if fully set forth. In this disclosure, it is pointed out that for an AODLF device, there is a minimum of the Bragg angle of incidence with frequency and that the Bragg angle of a diffraction varies in a substantially linear manner with changes in frequency.

Turning now to FIG. 5, an element for the use one embodiment of improved system for remote chemical analysis of this invention is shown in several embodiments. The combined acousto-optic device with fiber-optic connectors is shown in the structure indicated by the reference character 71. The structure 71 includes a housing 73 which supports the acousto-optic device 23 therein. As can be seen the transducer 37 is coupled to the RF drive means by means of an RF connector 75 on the external housing 73. Fiber-optic couples 77 and 79 are disposed on opposite sides of the housing 73 so as to be in direct communication with the input and output faces respectively of the acousto-optic device 23. The fiber-optic connectors 77 and 79 are commercially available. As can be see in the schematic representations of FIGS. 5A, 5B, 5C and 5D, several internal configurations of this device are possible.

Figure 5A:
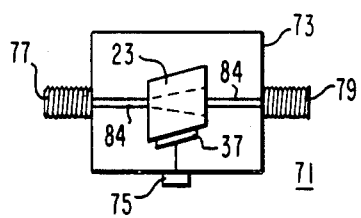
FIGS. 5A, B, C and D are illustrations of the design of an acousto-optic device with fiber optic connectors.
Figure 5B:
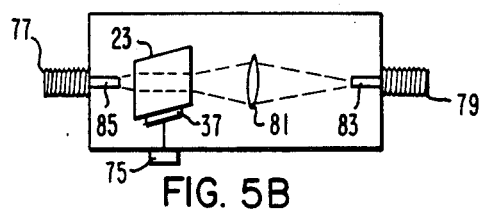
Figure 5C:
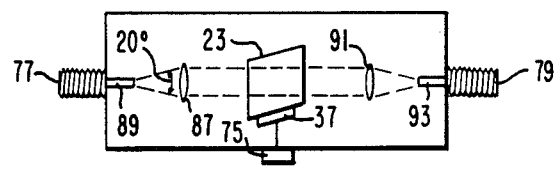
Figure 5D:
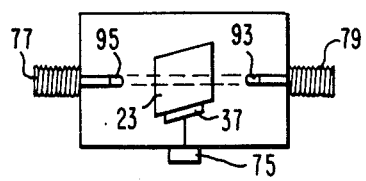

In FIG. 5A, both the input and output fiber-optic members 84 are butted up to the crystal input and output faces respectively. Infrared transmissive cement can also be employed to mate the optical fibers with the crystal. In FIG. 5B, the fiber-optic member 85 is spaced from the acousto-optic device 23. It can typically be expected that the output light from the fiber-optic member has a spread of roughly 20. This spread however has no adverse affect on the resolution of the acousto-optic device. A lens 81 is disposed adjacent the output face of the crystal 23 to match the acceptance angle of the fiberoptic member 83 with the acousto-optic device 23 output. The diffracted light is thus focused onto the focal plane defined at the fiber-optic member 83. The undiffracted light output of the acousto-optic device 23 is spatially separated on that focal plane. In the configuration shown in FIG. 5C, the first lens indicated at 87 would serve to collimate the light output from the fiber 89 while a second lens 91 near the output face of the crystal 23 would serve to focus the diffracted light onto the cable 93. Finally, in FIG. 5D graded index lenses 95 and 93 which are dimensioned for use with fiber optics and commercially available under the trademark SELFOC from Nippon Glass can be employed in lieu of the more conventional lenses described above in connection with FIGS. 5B and 5C. Accordingly, it should be appreciated that in the embodiments shown in FIGS. 1–3, the acousto-optic device 23 and associated lenses are representative of the apparatus 71 shown in FIG. 5. Thus the various combinations of both graded index lenses as well as more conventional lenses and fiber optics can be used in this apparatus to achieve the desired result.

EXPERIMENTAL USE

Figure 6:
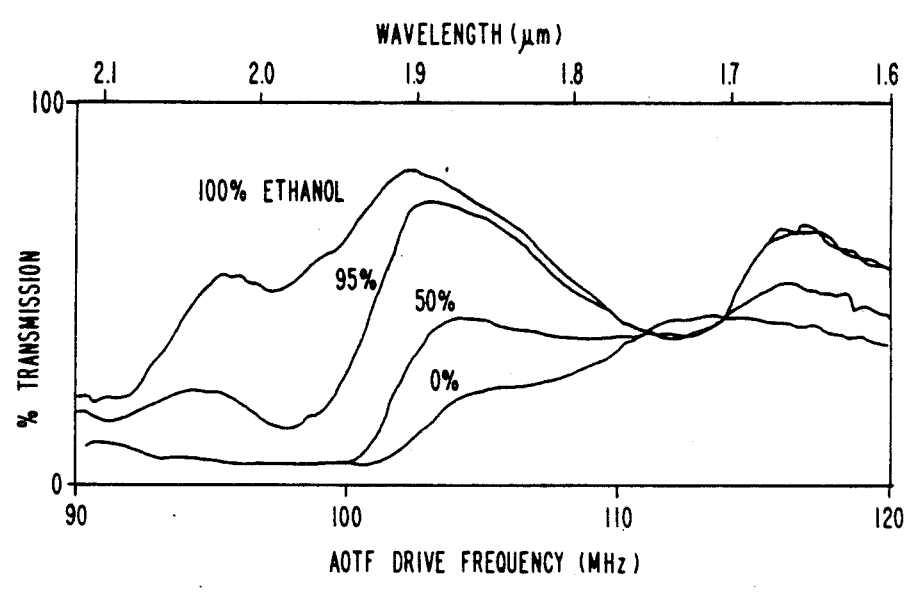
FIG. 6 is a graph presenting the percent of transmission for various concentrations of ethanol in water.
Figure 7:
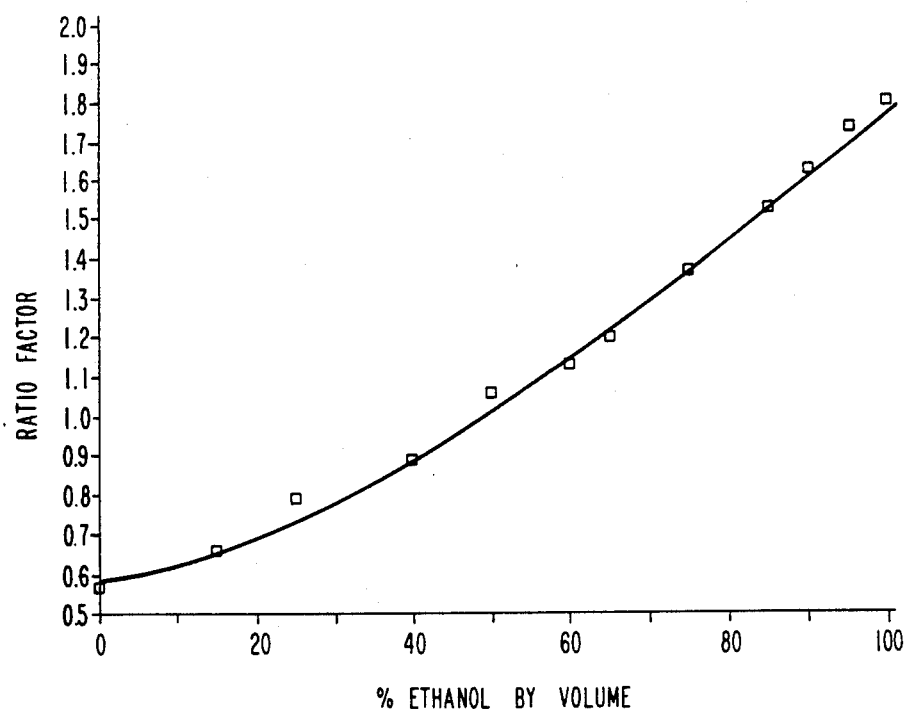
FIG. 7 is a graph presenting a calibration curve base on data obtained through a system of this invention.
Figure 8:
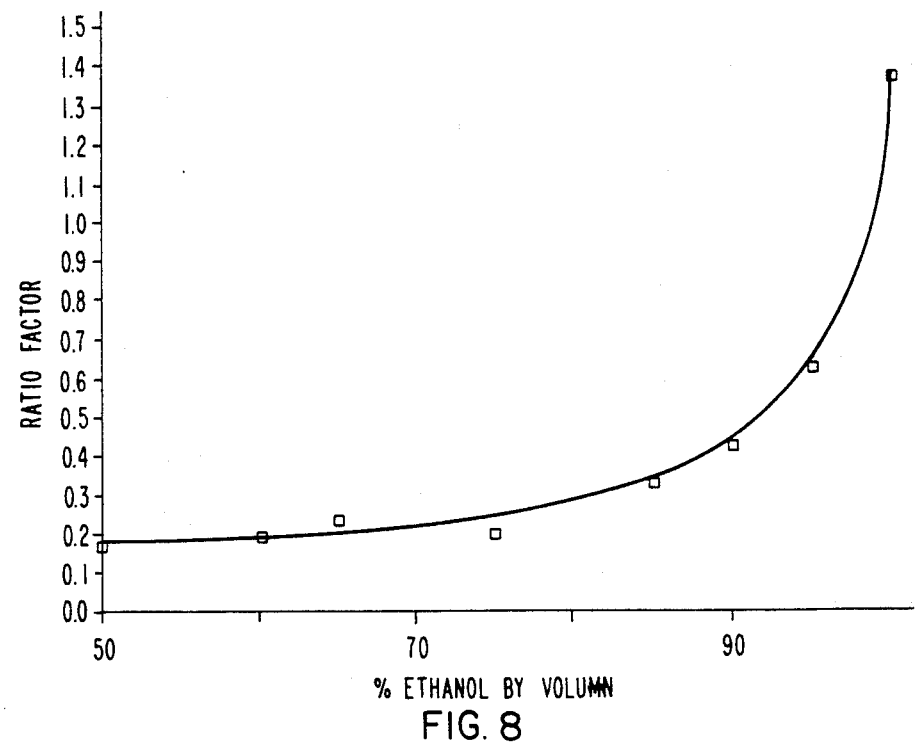
FIG. 8 is a graph presenting the calibration curve for concentrations of ethanol above 75%.

The system as discussed in conjunction with FIGS. 1 and 4 was tested by determining the concentration of ethanol in an ethanol-water mixture. A reference spectrum against which all further spectra were normalized and ratioed was first established by testing the system with no sample in the sample cell. After a system response was obtained, samples of various concentrations of ethanol in water mixtures were analyzed. Their spectra were ratioed and stored. A simple algorithm was developed to indicate the percentage of ethanol in the mixtures and at the same time cancel out some of the effects upon the data from the system. Such effects would include a dropoff at longer wavelengths which can be attributed to the reduced output of the halogen bulb and, in a small part, to the attenuation of quartz fibers. It should be obvious that additional algorithms can be utilized to compensate for these factors. In each case, during the testing, the spectral transmission for an ethanol and water mixture was obtained and then ratioed against the reference spectrum. This resulted in the percent transmission of light throughout the wavelength range measured with respect to an empty cell. The percent transmission for a pure ethanol, a 50% ethanol and a pure water mixture was shown in FIG. 6. It can be seen from these spectra that the transmission at 105 MHz rose evenly with an increase in the percent ethanol, while the transmission at 113 MHz dropped slightly. The algorithm involved taking the ratio of the percent transmission at these frequencies to each other, and using this ratio to determine the percent of ethanol. Data was gathered over a wide range of concentrations and the resulting calibration curve is shown in FIG. 7. It was also seen in the spectra that in connections of ethanol greater than 75%, it was more accurate to observe the ratio between 95 MHz and 113 MHz. The transmission rose sharply at 95 MHz as the water became more dilute, due to a very strong absorption by water at the corresponding wavelength of light. The calibration curve for concentrations of ethanol above 75% is shown in FIG. 8. The system could conceivably be programmed to switch to this more accurate ratio when it detected concentrations above a minimum limit by the first method.

As a test of the algorithm, several samples from a household liquor cabinet were obtained for analysis. The mixtures selected were relatively clear and covered the range from 12 to 47% ethanol content by volume. The spectra from these samples were obtained and analyzed as above, and the resolution ratios were used to estimate the percent alcohol in the mixture, based on a least square exponential curve fit of the calibration data. The results of the unknown and the estimated percentages are given in Table I.

TABLE I

DETERMINATION OF UNKNOWNS
Calibration formula: % Ethanol - 85.8 ln 1.76 (Ratio 105/113 MHz)

| Unknown | Determined Ratio Percentage of % transmission at 105 MHz/113 MHz | Predicted Percentage Ethanol | Ethanol by label |
|---|---|---|---|
| Gordon's Gin | 1.016 | 49.4 | 47 |
| Bacardi Rum | .932 | 42.5 | 40 |
| Heublein Gin | .890 | 38.6 | 34 |
| M&R Vermouth | .730 | 21.6 | 18 |
| Keknyelu White Wine | .693 | 17.1 | 12 |

The calculated percentages of these samples were slightly higher than the listed percentages given on the labels, which could result in several factors. First, the examples examined were not pure ethanol and water mixtures, although samples as close to this as possible were used. The most significant offset in the data was at the lower percentages. These samples were white wines, which have a greater amount of contaminants and are less strictly measured for alcohol content than higher ethanol content beverages. Unfortunately, no samples above 50% ethanol were readily available, although we expect results from such mixtures to have a higher accuracy.

The use of an AOTF in combination with a chromatographic column for the detection and the quantitative analysis of a species of interest is described in conjunction with the remaining figures and with reference to the forgoing.

Figure 9:
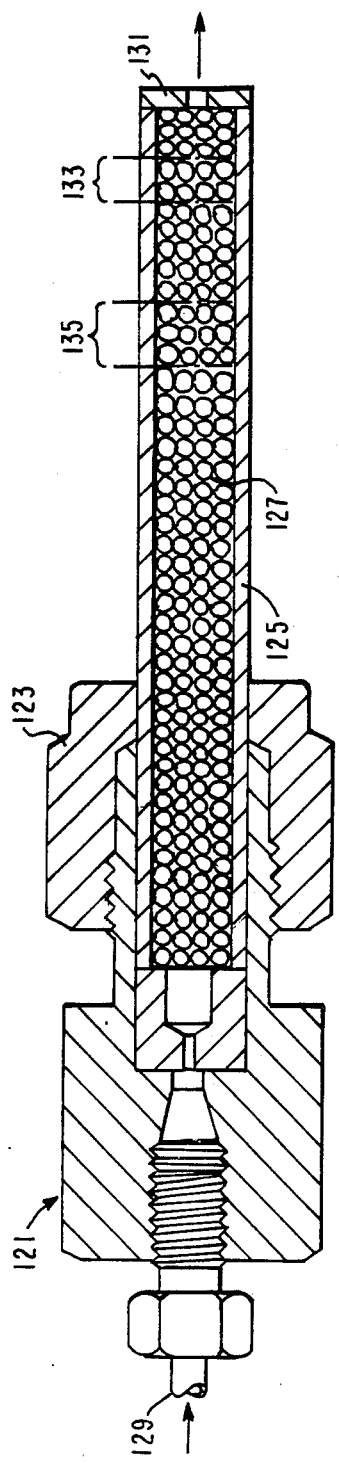
FIG. 9 is a cross section of a typical chromatographic column.
Figure 10:
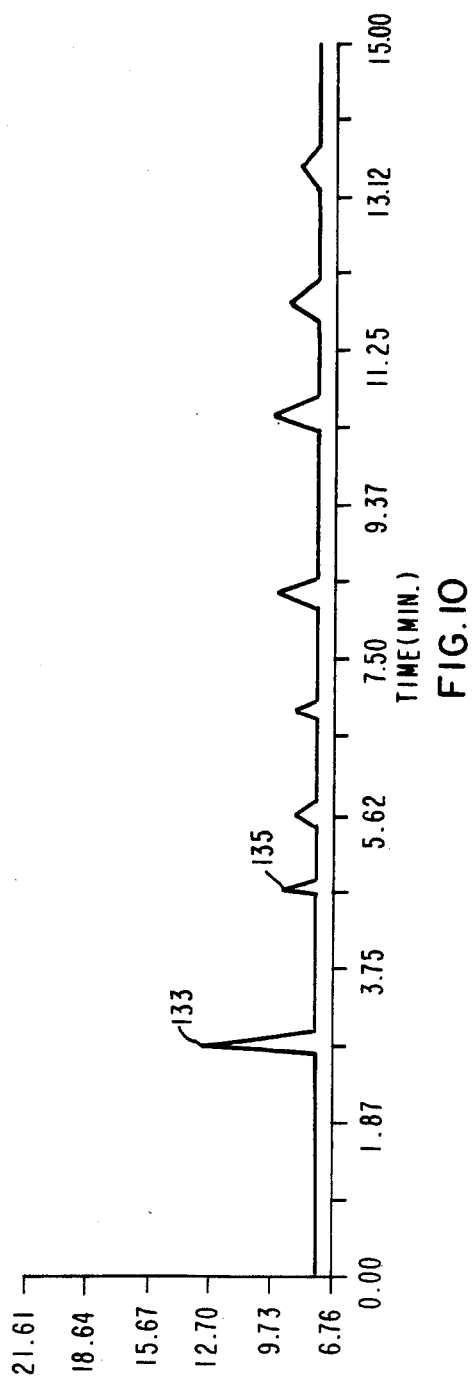
FIG. 10 is a chromatogram.
Figure 11:
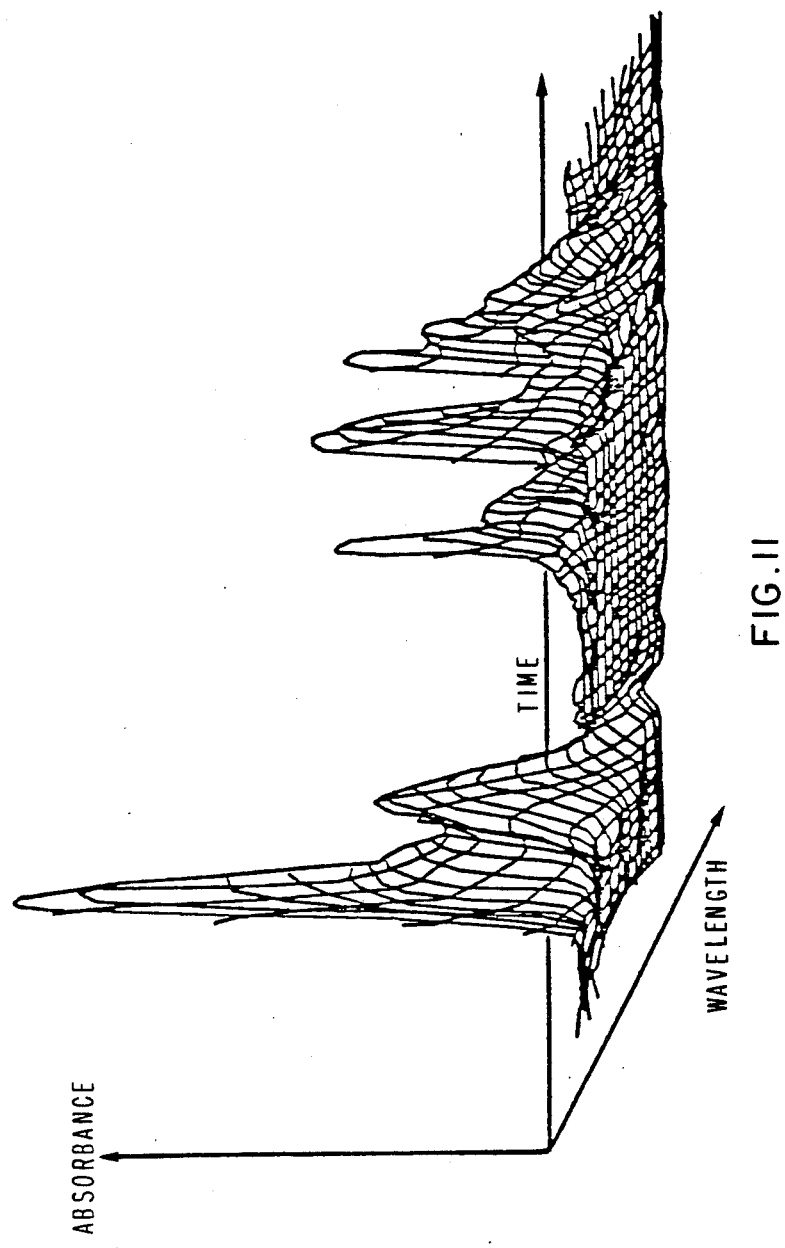
FIG. 11 is a chromatogram including spectral dependence.
Figure 12:
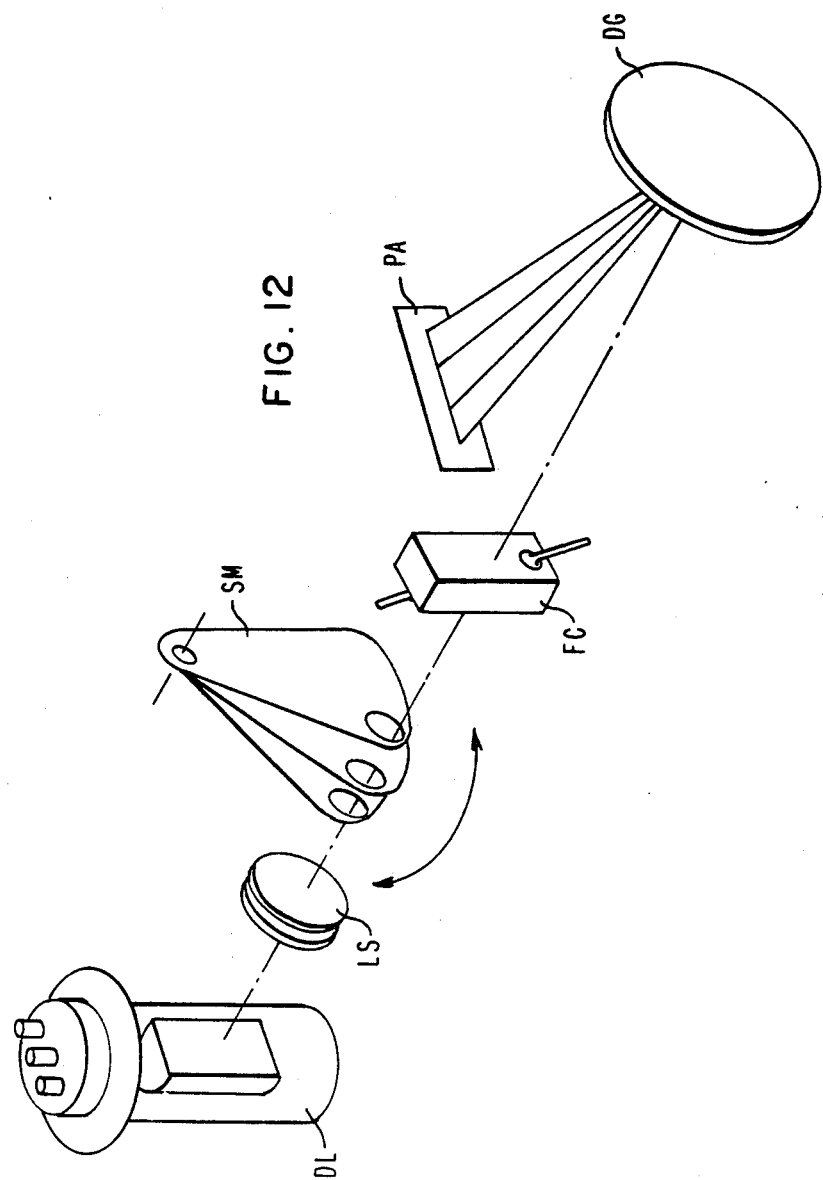
FIG. 12 is a schematic representation of a prior art system for measuring the spectral dependence of optical absorbance.

FIG. 9 shows the construction details of a typical column generally indicated by the reference character 121 and having a housing 123. A column 125 contains a suitable material 127 selected on the basis of the mixture to be separated by passage through the column 125. The mixture enters the column at one end 129, passes through the column's porous silica packing material 127 under pressure and exits the column at the other end 131. The separated species diffuse at different rates from the column and arrive at different times at the flow cell (113 of FIG. 15). The physical and temporal separation of the species by the column 121 is schematically represented in FIG. 9 and is graphically shown in FIG. 10 by means of the reference characters 133 and 135 which represent two separate species. If one can quickly perform optical measurements such as absorption or fluorescence emission spectral dependence, characteristic identifying features of each specie may be obtained before the next specie arrives at the detector. As shown on FIG. 11, if the spectral dependence of each specie can be measured at the detector, specie identification is possible by means of either absorbance or fluorescence emission.

Figure 14:
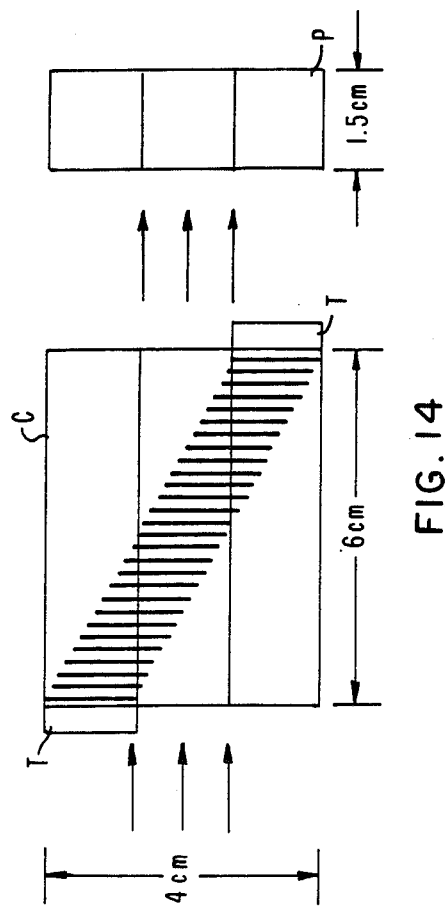
FIG. 14 illustrates a typical quartz AOTF design.

FIG. 14 illustrates a typical quartz AOTF crystal "C" design in which light to be analyzed or tuned enters from the left through an input polarizer (not shown), and tuned light exits from the right and passes through a polarizer "P". Tuning from 200 to 600 nm is accomplished by applying the appropriate drive RF to the transducers "T" mounted on the crystal "C". The acoustic waves produce the desired diffraction in the crystal.

Figure 15A:
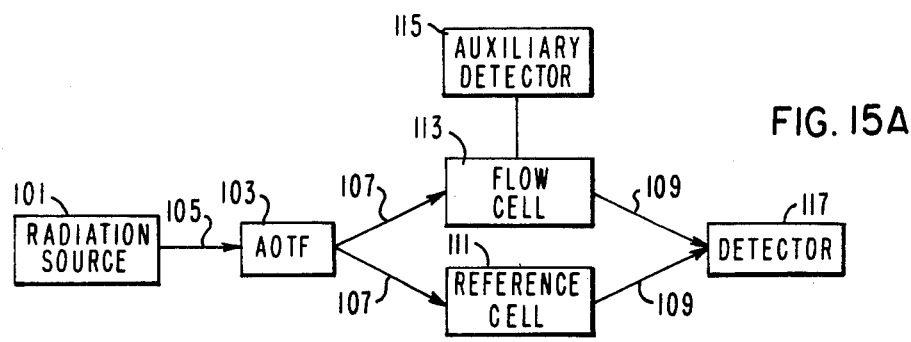
FIGS. 15A, B, C and D illustrate in block diagrammatic form several embodiments of the invention.
Figure 15B:
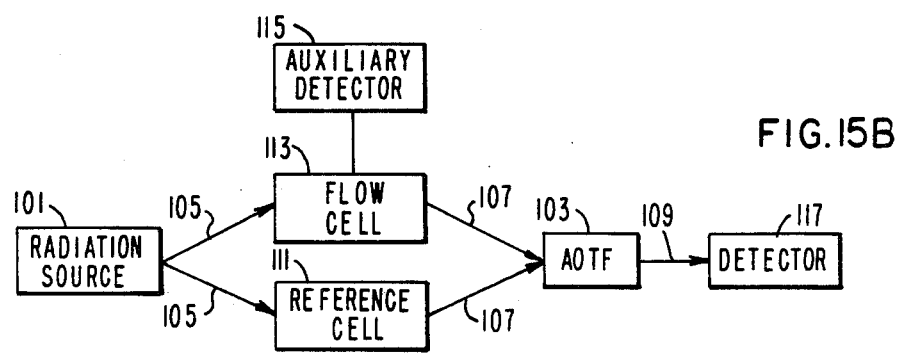
Figure 15C:
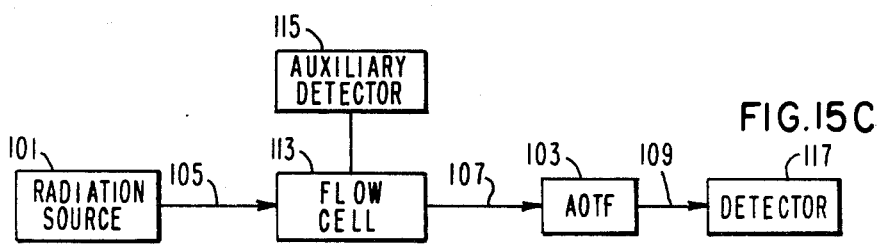

The chromatographic-AOTF apparatus of this invention provides an improved system for remote chemical analysis. A block diagram of several embodiments of this system are shown in FIGS. 15A, B, C and D. The system shown in FIG. 15A was prepared as a model in order to test the feasibility of this concept. The block diagrammatic system shown in FIG. 15B represents a preferred embodiment utilizing an AOTF for commercial application. FIG. 15C illustrates a further alternative embodiment with an AODLF and detector array. It should be appreciated that each embodiment provides an extremely useful improved system for remote chemical analysis.

Turning now to FIG. 15 where like reference characters represent equivalent components, various embodiments of the use of AOTF devices for performing optical measurements on the exiting specie from a chromatographic column are schematically represented. In all of these embodiments, the radiation source 101 is any suitable source of light in the wavelength range desired. In the ultraviolet it might be a deuterium discharge lamp, a xenon lamp, or a quartz/halogen/tungsten bulb, for example. In the visible to near infrared it could be a quartz/halogen/tungsten bulb, in the near to far infrared it could be a silicon carbide "Globar". The AOTF 103 would be constructed of a material suitable for the wavelength desired. For example, in the ultraviolet it could be a quartz AOTF, in the visible to near infrared it could be a tellurium dioxide AOTF, in the near to far infrared it could be a thallium arsenic selenide AOTF, for example. The means of coupling optical energy between the various components, 105, 107 and 109, could be fiber optics in many cases, or suitable combinations of lenses, mirrors, and beam splitters. The reference cell, 111, is simply an optical path not containing the species from the column. It is used to perform "differential absorption" spectroscopy where the difference in optical signals between the reference and sample containing "flow" cell paths is used as a measure of absorption. It could optically resemble the flow cell or it could simply be a second optical path not passing through the flow cell, such as the means 105, 107 or 109. It is possible to eliminate reference cell 111 when great accuracy is not required in the measurement. The flow cell 113 is any suitable cell, transparent to the radiation involved in the measurement, through which the species exiting from the column pass. The auxiliary detector 115 may or may not be present. In some cases two or more simultaneous types of measurements may be desired in order to better specify the exiting specie. For example, in addition to optical absorption it also may be desired to measure the specie of interest with an electron capture detector so that halogenated compounds can be additionally distinguished.

The detector 117 is any detector suitable for the wavelength range of the desired measurement. Suitable detectors for the ultraviolet to near infrared would be photomultiplier tubes or photodiodes, for example. In the near infrared an indium antimony, lead sulfide, or lead selenide photodiode or photoconductor could be used. In the farther infrared mercury cadmium telluride photodiodes or photoconductors could typically be used. Not shown on FIG. 15 are the various peripheral optical accessories which could also be added if desired, such as band-pass filters and optical apertures. Typical combinations of components are shown on FIG. 15 for performing the optical measurements.

The embodiment illustrated in FIG. 15A provides a system for performing optical absorption. Broad radiation from the source 101 is selectively tuned by the AOTF 103 to the various wavelengths desired. The tuned light is passed through the flow cell 113 where the attenuation due to the specie is determined by comparing the intensity of light exiting from 113 relative to the reference light from 111. The difference between these signals is compared at the detector 117.

The embodiment illustrated in FIG. 15B provides an alternative configuration for performing optical absorption. The board radiation from the source is passed through both the flow cell and the reference cell and the difference between these two intensities at various wavelengths is then analyzed by the AOTF and following detector.

The embodiment of FIG. 15C is an apparatus for determining the wavelength dependence of the fluorescence emitted by certain species when excited with the proper wavelength of light, usually short wavelength ultraviolet. In this case the radiation source 101 is used only to excite the fluorescence of the sample in the flow cell 113. Suitable filters may be used with the source to restrict its radiation to the proper wavelength interval so that its output only excites fluorescence and does not interfere with the fluorescence wavelengths. The fluorescence wavelength distribution is then analyzed with the AOTF and following detector.

Figure 15D:
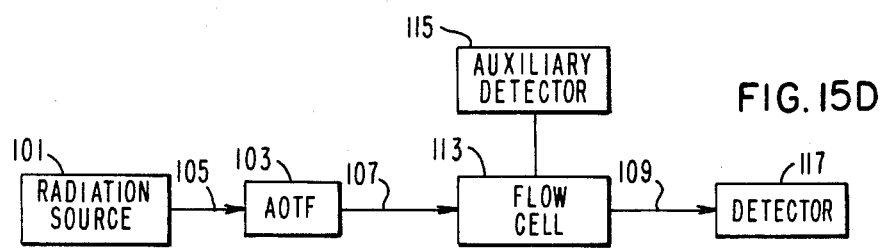

The embodiment shown in FIG. 15D provides an apparatus method for determining the excitation spectrum of the fluorescence, that is, the relative efficiency with which various exciting wavelengths can excite the fluorescence. In this case the broad wavelength radiation from the source 101 is progressively tuned to various wavelengths and the relative intensity of the fluorescence versus wavelength is monitored at the detector. A bandpass filter is typically placed in front of the detector to pass only the fluorescence wavelengths and block others.

The embodiments of FIGS. 15C and 15D could of course be combined to provide an apparatus whereby combined absorption and fluorescence measurements could also be accomplished. A large variety of combinations of components could be utilized but the above examples show the possibilities of this approach.

What has been described is both a system and a technique for improved quantitative chemical analysis. The invention provides for the use of a solid-state acoustooptic device in combination with a chromatographic column in order to provide a system for both the detection and the quantitative chemical analysis of a species of interest. An acousto-optic tunable filter spectral analyzer connected to a separate "in-line" sensor is used to measure a specie of interest in a mixture. While modifications and improvements to this system are planned, the feasibility of such a system has been established. The composition of liquid or concentrated gas samples can be examined in cell safely removed from the electrical system by fiber optics. The absence of electricity near the sensing cell negates the need for expensive enclosures for the sensor, making this device highly suited to industries such as petroleum processing. In addition, the solid-state construction of the AOTF system lowers the chance of both misalignment and component wear.

We claim:

1. An improved system for quantitative chemical analysis comprising:
    a chromatographic column means into which a mixture is introduced and through which individual specie of the mixture diffuse at various rates so that each single emerging specie is temporally separated from each other specie and has identifiable characteristics;

a radiation source of a predetermined range of wavelengths in optical communication with the single emerging specie by means of a first optical path whereby radiation from said radiation source is modified by the identifiable characteristics;

a detection means disposed in optical communication with the single emerging specie by means of a second optical path whereby the modified radiation is detected and a first output signal reflective of the detected radiation is generated;

an acousto-optic tunable filter system, which system comprises an acousto-optic tunable filter having an optically aligned acousto-optic crystal disposed in one of said first or second optical paths so as to be in optical alignment therewith such that the radiation is passed through the crystal at a predetermined angle relative to the crystal's optic axis, an acoustic transducer means coupled to a variable frequency RF energy source and to the crystal to launch acoustic waves into the crystal to interact with a selected narrow bandwidth portion of the radiation to make it distinguishable from the remaining radiation which selected narrow bandwidth portion is a function of the frequency of the RF energy and the acoustic waves;

computing means to which the detection means output signal is applied for determining the emerging specie by the identifiable characteristics; and, a parallel optical path defining thereby a reference cell means whereby radiation passes through both the first and second optical paths and said parallel optical path to the detection means whereby a second output signal reflective of the detected radiation passing through said parallel optical path is generated and wherein the acousto-optic crystal is also disposed in said parallel optical path.

2. The improved system for quantitative chemical analysis according to claim 1 wherein the acousto-optic tunable filter crystal is crystalline quartz (SiO2).

3. The improved system for quantitative chemical analysis according to claim 1 wherein the acousto-optic tunable filter crystal is thallium arsenic selenide (TAS).

4. The improved system for quantitative chemical analysis according to claim 1 wherein the acousto-optic tunable filter crystal is tellurium dioxide (TeO2).

5. The improved system for quantitative chemical analysis according to claim 1 wherein the first and second optical paths comprise optical fiber means.

6. The improved system for quantitative chemical analysis according to claim 1 wherein the first and second optical paths are defined by means including lens means, mirror means, and beam splitter means.

7. The improved system for quantitative chemical analysis according to claim 1 wherein the aotf is disposed in the first optical path.

8. The improved system for quantitative chemical analysis according to claim 1 wherein the aotf is disposed in the second optical path.

9. The improved system for quantitative chemical analysis according to claim 1 including an auxiliary detector means responsive to the emerging specie and in fluid communication with the chromatographic column means.

10. The improved system for quantitative chemical analysis according to claim 1 wherein the computing means is also responsive to the second output signal and wherein the difference between the first and second optical represents a measure of the emerging specie's absorption characteristic.

11. The improved system for quantitative chemical analysis according to claim 1 including an auxiliary detector means responsive to the emerging specie and in fluid communication with the chromatographic column means.

12. The improved system for quantitative chemical analysis according to claim 1 wherein the aotf is disposed in the first optical path.

13. The improved system for quantitative chemical analysis according to claim 1 wherein the aotf is disposed in the second optical path.

14. The improved system for quantitative chemical analysis according to claim 1 wherein the acoustooptic tunable filter crystal is crystalline quartz (SiO2).

15. The improved system for quantitative chemical analysis according to claim 1 wherein the acousto-optic tunable filter crystal is thallium arsenic selenide (TAS).

16. The improved system for quantitative chemical analysis according to claim 1 wherein the acoustooptic tunable filter crystal is tellurium dioxide (TeO2).

17. An improved system for quantitative chemical analysis comprising:

a chromatographic column means into which a mixture is introduced and through which individual specie of the mixture diffuse at various rates so that each single emerging specie is temporally separated from each other specie and has identifiable characteristics;

a radiation source of a predetermined range of wavelengths in optical communication with the single emerging specie by means of a first optical path whereby radiation from said radiation source is modified by the identifiable characteristics;

a detection means disposed in optical communication with the single emerging specie by means of a second optical path whereby the modified radiation is detected and a first output signal reflective of the detected radiation is generated;

an acousto-optic tunable filter system, which system comprises an acousto-optic tunable filter having an optically aligned acousto-optic crystal disposed in said first optical path so as to be in optical alignment therewith such that the radiation is passed through the crystal at a predetermined angle relative to the crystal's optic axis, an acoustic transducer means coupled to a variable frequency RF energy source and to the crystal to launch acoustic waves into the crystal to interact with a selected narrow bandwidth portion of the radiation to make it distinguishable from the remaining radiation which selected narrow bandwidth portion is a function of the frequency of the RF energy and the acoustic waves;

a parallel optical path defining thereby a reference cell means whereby radiation passes through both the first and second optical paths and said parallel optical path to the detection means whereby a second output signal reflective of the detected radiation passing through said parallel optical path is generated and wherein the acousto-optic crystal is also disposed in said parallel optical path; and computing means to which the detection means output signal is applied for determining the emerging specie by the identifiable characteristics and said computing means also being responsive to the second output signal and wherein the difference between the first and second optical represents a measure of the emerging specie's absorption characteristic.

18. The improved system for quantitative chemical analysis according to claim 17 including an auxiliary detector means responsive to the emerging specie and in fluid communication with the chromatographic column means.

19. The improved system for quantitative chemical analysis according to claim 17 wherein the acousto-optic tunable filter crystal is crystalline quartz ($SiO_2$).

20. The improved system for quantitative chemical analysis according to claim 17 wherein the acoustooptic tunable filter crystal is thallium arsenic selenide (TAS).

21. The improved system for quantitative chemical analysis according to claim 17 wherein the acousto-optic tunable filter crystal is tellurium dioxide ($TeO_2$).

22. The improved system for quantitative chemical analysis according to claim 17 wherein the first and second optical paths comprise optical fiber means.

23. The improved system for quantitative chemical analysis according to claim 17 wherein the first and second optical paths are defined by means including lens means, mirror means, and beam splitter means.

24. An improved system for quantitative chemical analysis comprising:
a chromatographic column means into which a mixture is introduced and through which individual specie of the mixture diffuse at various rates so that each single emerging specie is temporally separated from each other specie and has identifiable characteristics;
a radiation source of a predetermined range of wavelengths in optical communication with the single emerging specie by means of a first optical path whereby radiation from said radiation source is modified by the identifiable characteristics;
a detection means disposed in optical communication with the single emerging specie by means of a second optical path whereby the modified radiation is detected and a first output signal reflective of the detected radiation is generated;
an acousto-optic tunable filter system, which system comprises an acousto-optic tunable filter having an optically aligned acousto-optic crystal disposed in said second optical path so as to be in optical alignment therewith such that the radiation is passed through the crystal at a predetermined angle relative to the crystal's optic axis, an acoustic transducer means coupled to a variable frequency RF energy source and to the crystal to launch acoustic waves into the crystal to interact with a selected narrow bandwidth portion of the radiation to make it distinguishable from the remaining radiation which selected narrow bandwidth portion is a function of the frequency of the RF energy and the acoustic waves;
a parallel optical path defining thereby a reference cell means whereby radiation passes through both the first and second optical paths and said parallel optical path to the detection means whereby a second output signal reflective of the detected radiation passing through said parallel optical path is generated and wherein the acousto-optic crystal is also disposed in said parallel optical path; and
computing means to which the detection means output signal is applied for determining the emerging specie by the identifiable characteristics, said computing means also being responsive to the second output signal and wherein the difference between the first and second optical represents a measure of the emerging specie's absorption characteristic.

25. The improved system for quantitative chemical analysis according to claim 24 including an auxiliary detector means responsive to the emerging specie and in fluid communication with the chromatographic column means.

26. The improved system for quantitative chemical analysis according to claim 24 wherein the acoustooptic tunable filter crystal is crystalline quartz ($SiO_2$).

27. The improved system for quantitative chemical analysis according to claim 24 wherein the acoustooptic tunable filter crystal is thallium arsenic selenide (TAS).

28. The improved system for quantitative chemical analysis according to claim 24 wherein the acoustooptic tunable filter crystal is tellurium dioxide ($TeO_2$).

29. The improved system for quantitative chemical analysis according to claim 24 wherein the first and second optical paths comprise optical fiber means.

30. The improved system for quantitative chemical analysis according to claim 24 wherein the first and second optical paths are defined by means including lens means, mirror means, and beam splitter means.

31. An improved system for quantitative chemical analysis comprising:
a chromatographic column means into which a mixture is introduced and through which individual specie of the mixture diffuse at various rates so that each single emerging specie is temporally separated from each other specie and has identifiable characteristics;
a radiation source of a predetermined range of wavelengths in optical communication with the single emerging specie by means of a first optical path whereby radiation from said radiation source is modified by the identifiable characteristics;
a detection means disposed in optical communication with the single emerging specie by means of a second optical path whereby the modified radiation is detected and a first output signal reflective of the detected radiation is generated;
an acousto-optic dispersive light filter (AODLF) system, which system comprises an optically birefringenet crystal having an optical input face, and an optical output face, the input face being disposed at a predetermined angle which is normal to the incident radiation in one of said first or second optical paths, an acoustic transducer means coupled to a variable frequency RF energy source and to the crystal to launch acoustic waves into the crystal at a predetermined fixed frequency wherein each wavelength resolution element which emerges from the optical output face is at a different diffracted angle, and wherein the predetermined angle of the optica input face is selected such that for the fixed acoustic frequency, there is a minimum in the Bragg angle with frequency, while the diffracted Bragg angle increases linearly with frequency;
computing means to which the detection means output signal is applied for determining the emerging specie by the identifiable characteristics; and,
a parallel optical path defining thereby a reference cell means whereby radiation passes through both the first and second optical paths and said parallel optical path to the detection means whereby a second output signal reflective of the detected radiation passing through said parallel optical path is generated and wherein the acousto-optic crystal is also disposed in said parallel optical path.

32. The improved system for quantitative chemical analysis according to claim 31 wherein the computing means is also responsive to the second output signal and wherein the difference between the first and second optical represents a measure of the emerging specie's absorption characteristic.

33. The improved system for quantitative chemical analysis according to claim 31 including an auxiliary detector means responsive to the emerging specie and in fluid communication with the chromatographic column means.

* * * * *